(12) United States Patent
Chen et al.

(10) Patent No.: US 10,815,253 B2
(45) Date of Patent: Oct. 27, 2020

(54) PREPARATION METHOD FOR ZEOLITIC IMIDAZOLATE FRAMEWORKS

(71) Applicant: China University of Petroleum-Beijing, Beijing (CN)

(72) Inventors: Guangjin Chen, Beijing (CN); Bei Liu, Beijing (CN); Hai Li, Beijing (CN); Mingke Yang, Beijing (CN); Changyu Sun, Beijing (CN); Wan Chen, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 0 days.

(21) Appl. No.: 16/459,443

(22) Filed: Jul. 1, 2019

(65) Prior Publication Data
US 2020/0291046 A1   Sep. 17, 2020

(30) Foreign Application Priority Data

Mar. 12, 2019  (CN) .......................... 2019 1 0183203

(51) Int. Cl.
C07F 3/06 (2006.01)
C07D 235/06 (2006.01)
C07D 233/56 (2006.01)
C07F 15/06 (2006.01)

(52) U.S. Cl.
CPC .............. *C07F 3/06* (2013.01); *C07D 233/56* (2013.01); *C07D 235/06* (2013.01); *C07F 15/06* (2013.01)

(58) Field of Classification Search
None
See application file for complete search history.

(56) References Cited

U.S. PATENT DOCUMENTS

2007/0202038 A1   8/2007  Yaghi et al.
2013/0197235 A1   8/2013  Thompson et al.

FOREIGN PATENT DOCUMENTS

| CN | 102731538 B | 12/2015 |
| CN | 105597706 B | 12/2017 |
| CN | 105985362 B | 6/2018 |

OTHER PUBLICATIONS

Kyo Sung Park et al., Exceptional chemical and thermal stability of zeolitic imidazolate frameworks, PNAS, Jul. 5, 2006, vol. 103, No. 27, pp. 10186-10191.
Xiao-Chun Huang et al., Ligand-Directed Strategy of Zeolite-Type Metal-Organic Frameworks: Zinc (II) Imidazolates with Unusual Zeolitic Topologies, Angewandte Chemie, 2006, vol. 45, pp. 1557-1559.
Yichang Pan et al., Rapid synthesis of zeolitic imidazolate framework-8 (ZIF-8) nanocrystals in an aqueous system, The Royal Society of Chemistry 2011, vol. 47, pp. 2071-2073.
Qi Shi et at., Synthesis of ZIF-8 and ZIF-67 by Steam-Assisted Conversation and an Investigation of Their Tribological Behaviors, Angewandte Chemie, 2011, vol. 50, pp. 672-675.
Adam F. Gross et al., Aqueous room temperature synthesis of cobalt and zinc sodalite zeolitic imidizoate frameworks, Dalton Transactions, 2012, vol. 41, pp. 5458-5460.
Jonosch Cravillon et al., Controlling Zeolitic Imidazolate Framework Nano- and Microcrystal Formation: Insight into Crystal Growth by Time-Resolved In Situ Static Light Scattering, ACS Publications, 2011, vol. 23, pp. 2130-2141.
Jianfeng Yao et al., High-yield synthesis of zeolitic imidazolate frameworks from stoichiometric metal and ligand precursor aqueous solutions at room temperature, CrystEngComm, 2013, vol. 15, pp. 3601-3606.
Yi-nan Wu et al., Amino acid assisted templating synthesis of hierarchical zeolitic imidazolate framework-8 for efficient arsenate removal, Nanoscale, 2014 vol. 6, pp. 1105-1112.
Patrick J. Beldon et al., Rapid Room-Temperature Synthesis of Zeolitic Imidazolate Frameworks by Using Mechanochemistry, Angewandte Chemie, 2010, vol. 49, pp. 9640-9643.
Li Sze Lai et al., Fast Synthesis of Highly Crystalline ZIF-8 using Microwave-assisted Solvothermal Method, School of Chemical Engineering, Universiti Teknologi Petronas, Applied Mechanics and Materials, 2015, vols. 773-774, pp. 1133-1137.
Hye-Young Cho et al., High yield 1-L scale synthesis of ZIF-8 via a sonochemical route, Microporous and Mesoporous Materials, 2012, vol. 169, pp. 180-184.
Maximilian Hovestadt et al., Synthesis of the zeolitic imidazolate framework FIF-4 from the ionic liquid 1-butyl-3-methylimidazolium umidazolate, The Journal of Chemical Physics, 20, vol. 148, 6 pages.
Junfeng Qian et al., Hydrothermal synthesis of zeolitic imidazolate framework-67 (ZIF-67) nanocrystals, Materials Letters, 2012, vol. 82, pp. 220-223.
Xiongshi Tong, et al., Removal of CO2 from natural gas by 2-methylimidazole/ethylene glycol system at room temperature, CIESC Journal, 2016, vol. 67, No. 10, pp. 4240-4245.
Extended European Search Report dated Oct. 11, 2019 for counterpart European Patent Application No. 19180497.0, 9 pages.
Search Report in corresponding Chinese Patent Application No. 201910183203.1 dated Mar. 25, 2020.
Dffice Action in corresponding Chinese Patent Application No. 201910183203.1 dated Mar. 25, 2020.

*Primary Examiner* — Joseph R Kosack
(74) *Attorney, Agent, or Firm* — Loza & Loza, LLP; Michael F. Fedrick (57) ABSTRACT

The present invention provides a preparation method for zeolitic imidazolate frameworks. The preparation method comprises: adding a metal carbonate or oxide, an organic ligand to a hydrophilic liquid to obtain a mixture; introducing an acidic gas to reach a reaction pressure of 0.1 MPa to 2.0 MPa, and reacting for a predetermined time; heating to 30° C.-60° C. and vacuuming to obtain the zeolitic imidazolate framework. The present invention also provides a zeolitic imidazolate framework obtained by the above preparation method. The preparation method according to the present invention is environmentally friendly and has a high yield.

8 Claims, 6 Drawing Sheets

PREPARATION METHOD FOR ZEOLITIC IMIDAZOLATE FRAMEWORKS

FIELD OF THE INVENTION

The present invention relates to a preparation method of a zeolitic material, in particular to a method for preparing a zeolitic imidazolate framework, and belongs to the technical field of preparation of zeolitic materials.

BACKGROUND

Zeolitic imidazolate frameworks (ZIFs) are one of MOFs materials. They are a novel topological structure formed by transition metal ions connected with imidazole or derivatives thereof, and they not only have the advantages of large specific surface area, high porosity, large pore volume, adjustable cell size and modifiable framework, but also have good chemical and thermal stability, so they can be widely used in the fields of gas storage and separation, photochemical materials, magnetic materials, catalysis and medicine.

At present, the traditional synthesis method for ZIFs is to dissolve a nitrate containing metal ions ($Zn^{2+}/Co^{2+}$) in an organic solvent such as N,N-dimethylformamide (DMF), N,N-diethylformamide (DEF), or methanol, and then react with an imidazole or an imidazole derivative, followed by filtration, washing, and drying to obtain ZIFs material. In 2006 Yaghi (Yaghi et al, Exceptional chemical and thermal stability of zeolitic imidazolate frameworks, PNAS, 2006, 103 (27): 10186-10191) successfully synthesized a series of ZIFs (ZIF-1 to ZIF-12) by dissolving metal ($Zn^{2+}/Co^{2+}/In^{3+}$) nitrates in DMF, and controlling the molar ratio of different metals to organic ligands at a reaction temperature of 85° C. to 140° C. for a reaction time of 24 to 96 hours, as shown in Table 1. In this process, the solvent acts as a templating agent or a structure directing agent, and the high temperature condition is more favorable for the dissolution of the ligand. This method can obtain regular single-phase crystals, but has the following disadvantages: high reaction temperature, long reaction time, high energy consumption and cost; high solvent consumption and low yield; unrecyclable metal salt anions, and poor environmental friendliness. Chen et al. (Chen et al, Ligand-Directed Strategy for Zeolite-Type Metal-Organic Frameworks: Zinc(ii) Imidazolates with Unusual Zeolitic Topologies, Angew. Chem. Int. Ed., 2006, 45: 1557-1559) successfully synthesized ZIF-8/ZIF-14 at room temperature by using zinc hydroxide as a zinc source, controlling the molar ratio of $Zn^{2+}$ to 2-methylimidazole/2-ethylimidazole at 1:2, and adding aqueous ammonia to methanol solvent. The yield reached 60%-70%, but there were also problems such as long reaction time (30 days).

TABLE 1

| Kind | Metal source | Organic ligand | Molar ratio | T/° C. | t/h | Additive | Yield |
|---|---|---|---|---|---|---|---|
| ZIF-1 | Zinc nitrate tetrahydrate | Imidazole | 6.47 | 85 | 24 | — | 17% |
| ZIF-2 | Zinc nitrate tetrahydrate | Imidazole | 15.13 | 85 | 72 | — | — |
| ZIF-3 | Zinc nitrate tetrahydrate | Imidazole | 11.54 | 85 | 96 | NMP[a] | — |
| ZIF-4 | Zinc nitrate tetrahydrate | Imidazole | 2.88 | 130 | 48 | — | 47% |
| ZIF-6 | Zinc nitrate tetrahydrate | Imidazole | 0.84 | 85 | 72 | — | — |
| ZIF-10 | Zinc nitrate tetrahydrate | Imidazole | 11.54 | 85 | 96 | — | — |
| ZIF-7 | Zinc nitrate tetrahydrate | Benzimidazole | 0.74 | 130 | 48 | — | 37% |
| ZIF-8 | Zinc nitrate tetrahydrate | 2-methylimidazole | 0.91 | 140 | 24 | — | 25% |
| ZIF-9 | Cobalt nitrate hexahydrate | Benzimidazole | 0.7 | 130 | 48 | — | 30% |
| ZIF-11 | Zinc nitrate tetrahydrate | Benzimidazole | 15.22 | 100 | 96 | — | 23% |
| ZIF-12 | Cobalt nitrate hexahydrate | Benzimidazole | 7.38 | 130 | 48 | — | — |
| ZIF-5[b] | Indium nitrate pentahydrate + Zinc nitrate tetrahydrate | Imidazole | 20:4:1 | 150 | 72 | Tetraethylammonium hydroxide | 70% |

Note:
— indicates null or no description in the literature;
[a]represents NMP as N-methylpyrrolidone;
[b]indicates that ZIF-5 is synthesized using DMF/n-butanol as a solvent.

In recent years, the method of synthesizing ZIFs with water as the reaction medium instead of organic solvent has attracted wide interest. The use of water as a reaction solvent can greatly reduce the synthesis cost and reduce the environmental impact. However, in order to obtain ZIFs with high purity, the requirement for the amount of organic ligand to be added is high. Pan et al. (Pan et al, Rapid synthesis of zeolitic imidazolate framework-8 (ZIF-8) nanocrystals in an aqueous system, Chem. Commun, 2011, 47:2071-2073) successfully synthesized ZIF-8 with a yield of 80% (based on the amount of zinc ions) by dissolving zinc nitrate hexahydrate and 2-methylimidazole at a molar ratio of 1:70 in water, and reacting for 5 minutes under stirring at room temperature. Shi et al. (Shi et al, Synthesis of ZIF-8 and ZIF-67 by steam-assisted conversion and an investigation of their tribological behaviors, Angew. Chem., Int. Ed., 2011, 50:672-675) used zinc acetate dihydrate as a zinc source and water as a reaction medium to synthesize a non-porous metal-organic hybrid by controlling the molar ratio of $Zn^{2+}$ to 2-methylimidazole at 1:10 and reacting at 120° C. for 24 hours, it had a density of 1.58 g·cm$^{-3}$, much larger than other ZIFs materials (for example, the density of ZIF-8 is 0.95 g·cm$^{-3}$). The above synthesis methods show that in the aqueous solution, when the organic ligand is much excessive with respect to the metal ($Zn^{2+}/Co^{2+}$) ions, the synthesis of the ZIFs material is facilitated. However, due to the presence of other by-product ions in the aqueous solution, the organic ligand is not recyclable, resulting in serious waste of pharmaceutical resources.

Later, researchers added organic amines or inorganic ammonium additives to the liquid medium as deprotonating agents, greatly reducing the amount of organic ligands to be used. Gross et al. (Gross et al, Aqueous room temperature synthesis of cobalt and zinc sodalite zeolitic imidizolate frameworks, Dalton Trans., 2012, 41:5458-5460) successfully synthesized ZIF-8/ZIF-67 by using zinc nitrate hexahydrate and cobalt nitrate hexahydrate as the metal source, adding triethylamine (TEA) to aqueous solution, controlling the molar ratio of $Zn^{2+}/Co^{2+}$ to 2-methylimidazole at 1:4 to 1:16 and reacting at room temperature for 10 minutes. Cravillon et al. (Cravillon et al, Controlling Zeolitic Imidazolate Framework Nano- and Microcrystal Formation: Insight into Crystal Growth by Time-Resolved In Situ Static Light Scattering, Chem. Mater, 2011, 23:2130-2141) synthesized ZIF-8 by adding n-butylamine to methanol solvent, reducing the molar ratio of zinc nitrate hexahydrate to 2-methylimidazole to 1:4, and reacting at room temperature for 24 hours. Yao et al. (Yao et al, High-yield synthesis of zeolitic imidazolate frameworks from stoichiometric metal and ligand precursor aqueous solutions at room temperature, Cryst Eng Comm, 2013, 15:3601-3606) successfully synthesized ZIF-8 and ZIF-67 by using zinc nitrate hexahydrate and cobalt nitrate hexahydrate as the metal source, adding nonionic surfactant triblock copolymer poly(ethylene oxide)-poly(propylene oxide)-poly(ethylene oxide) and ammonium hydroxide to the aqueous solution, reducing the molar ratio of $Zn^{2+}/Co^{2+}$ to organic ligand to 1:2, and reacting at room temperature for 10 minutes, and the yield was up to 98%. Li et al. (Li et al, Amino acid assisted templating synthesis of hierarchical zeolitic imidazolate framework-8 for efficient arsenate removal, Nanoscale, 2014, 6:1105-1112) successfully synthesized hierarchical zeolitic imidazolate framework ZIF-8 by adding amino acid (histidine/arginine) and cetyltrimethylammonium bromide cationic surfactant to the aqueous solution, with a molar ratio of zinc nitrate hexahydrate to 2-methylimidazole of 1:8, and reacting at room temperature for 12 hours, and the material had a meso- and micro-porous structure, which not only had a large mesopore volume, but also had an adjustable specific surface area. The above reports show that the addition of deprotonating agents reduces the amount of organic ligands to be used, but the composition of the liquid phase becomes complicated and by-products increase, failing to meet the requirements of economy and environmental protection.

Beldon et al. (Beldon et al. Rapid Room-Temperature Synthesis of Zeolitic Imidazolate Frameworks by Using Mechanochemistry, Angewandte Chemie-International Edition, 2010, 49(50):9640-9643) successfully synthesized ZIF-8 by using a mechanical milling method to control the molar ratio of zinc oxide to 2-methylimidazole at 1:2, and adding a small amount of N,N-dimethylformamide (DMF) and ammonium methanesulfonate accelerator and grinding for 30 minutes at room temperature. This method had a simple process (omitting the processes of filtration, centrifugation, etc.) and low production cost (omitting solvent). However, due to the addition of the accelerator such as ammonium methanesulfonate in the method, the product needs to be further purified, and if there is a solid phase reactant which cannot be completely converted, a solid-solid separation would be required, thereby increasing the potential defect of practical operation.

In addition, Lai et al. (Lai et al, Fast Synthesis of Highly Crystalline ZIF-8 using Microwave-assisted Solvothermal Method Applied Mechanics & Materials, 2015, 773-774: 1133-1137), based on conventional solvothermal synthesis, and used enhanced microwave-assisted synthesis, which could rapidly crystallize and nucleate, and greatly shorten the reaction time, so that ZIF-8 could be synthesized by reacting at 120° C. for only 0.5 hour. Cho et al. (Cho et al. High yield 1-L scale synthesis of ZIF-8 via a sonochemical route. Microporous and Mesoporous Materials. 2013, 169: 180-184) successfully synthesized ZIF-8 by employing a sonochemical synthesis route, adjusting the pH value of the organic solvent N,N-dimethylformamide (DMF) with NaOH and TEA, and reacting zinc nitrate hexahydrate with 2-methylimidazole at room temperature for 2 hours. This method utilizes ultrasonic waves to continuously generate bubbles inside the solvent, and with the growth and rupture of the bubbles, sound wave holes are formed, which can generate very high local high temperature and high pressure, thereby increasing the activity of the reactants; simultaneously the crystallization time can be greatly reduced, which helps to form a small crystal size and can greatly reduce the amount of organic solvent DMF to be used. However, the above two synthetic processes have strict synthesis conditions and complicated equipment requirements, so it is difficult to scale production.

Recently, Martin et al. (Martin et al, Synthesis of the zeolitic imidazolate framework ZIF-4 from the ionic liquid 1-butyl-3-methylimidazolium imidazolate, J. Chem. Phys., 2018, 148:193837) employed a novel ZIFs synthesis route, including firstly converting the organic ligand imidazole into an ionic liquid, dissolving the ionic liquid in an organic solvent, then adding zinc nitrate hexahydrate, and reacting at 130° C. for 48 hours, to successfully synthesize ZIF-4, and the yield was significantly higher than that of the traditional synthesis method (47%, 63%), as high as 77%-88%. However, this method has high reaction temperature, long time, complicated process, complicated operation, high energy consumption and high requirements on equipment.

In summary, existing synthetic methods all have their drawbacks. The conventional solvothermal method has a high reaction temperature, a long reaction time, unrecyclable solvent, and high energy consumption and synthesis cost. Although the use of water as a reaction solvent reduces the cost of the reaction solvent, it requires a large excess of ligand or addition of a proton-reducing agent to reduce the amount of ligand used, and does not meet the requirements of economy and environmental protection. Mechanical grinding, microwave-assisted synthesis, sonochemical synthesis, ionic liquid synthesis, etc. are difficult to popularize and industrialize, due to low purity, complicated equipment, and harsh process conditions.

SUMMARY OF THE INVENTION

In order to solve the above technical problems, an object of the present invention is to provide a method for preparing a zeolitic imidazolate framework which is environmentally friendly and has a high yield.

In order to achieve the above technical object, the present invention firstly provides a method for preparing a zeolitic imidazolate framework, comprising the following steps:

Step 1: adding a metal carbonate or oxide, an organic ligand to a hydrophilic liquid to obtain a mixture;

Step 2: introducing an acidic gas to reach a reaction pressure of 0.1 MPa to 2.0 MPa, and maintaining the pressure for 30 to 60 minutes, and terminating the reaction;

Step 3: heating to 30° C.-60° C. and vacuuming to obtain the zeolitic imidazolate framework.

The method for preparing a zeolitic imidazolate framework according to the present invention further comprises a step of post-treatment.

In a specific embodiment of the present invention, the post-treatment comprises filtering and separating the solid-liquid mixture after vacuuming in step 3 to obtain a solid phase product and a filtrate; and vacuum-drying and activating the solid phase product to obtain a ZIFs material. And the filtrate obtained by filtration can be recycled and reused as the hydrophilic liquid to synthesize a new zeolitic imidazolate framework.

The method for preparing a zeolitic imidazolate framework according to the present invention comprises the step of adding a metal carbonate or oxide, an organic ligand to a hydrophilic liquid to obtain a mixture. The resulting mixture may include precursors, unreacted metal carbonate or oxide, organic ligand.

In a specific embodiment of the present invention, step 1 is carried out at 10° C. to 40° C.

In a specific embodiment of the present invention, there is no particular requirement for the concentration of the hydrophilic liquid. The hydrophilic liquid to be used may be one or two or more of water, an alcohol and an amide.

For example, the hydrophilic liquid used may be an aqueous solution of an alcohol, an aqueous solution of an amide or an alcoholic solution of an amide.

In the preparation method according to the present invention, the liquid medium (hydrophilic liquid) may be water, which is inexpensive and has a low synthesis cost.

Specifically, the alcohol used may be methanol, ethanol, ethylene glycol, or triethylene glycol.

Further, the aqueous solution of the alcohol used may be an aqueous solution of methanol, an aqueous solution of ethanol, an aqueous solution of ethylene glycol, or an aqueous solution of triethylene glycol.

Specifically, the amide used may be N,N-dimethylformamide, N,N-dimethylacetamide or N,N-diethylformamide.

Further, the aqueous solution of the amide used may be an aqueous solution of N,N-dimethylformamide, an aqueous solution of N,N-dimethylacetamide, or an aqueous solution of N,N-diethylformamide.

Further, the alcoholic solution of the amide may be an alcoholic (methanol, ethanol, ethylene glycol or triethylene glycol) solution of N,N-dimethylformamide, N,N-dimethylacetamide or N,N-diethylformamide.

In a specific embodiment of the present invention, the metal carbonate or oxide used comprises one or two of basic zinc carbonate, cobalt carbonate, zinc oxide, and cobalt oxide.

When a metal carbonate or oxide is used, single metal ZIFs is prepared; when different metal carbonates or oxides are used, a bimetallic composite ZIFs can be prepared.

In a specific embodiment of the present invention, the organic ligand used is one or two or more of imidazole, 2-methylimidazole, 2-ethylimidazole, 2-propylimidazole, and benzimidazole.

When a single organic ligand is used, a single ligand ZIFs is prepared; when two or more organic ligands are used, a multi-ligand composite ZIFs can be prepared.

In a specific embodiment of the present invention, the molar ratio of the metal atoms in the metal carbonate or oxide used to the organic ligand is from 1:2 to 1:10. For example, the molar ratio of the metal atoms in the metal carbonate or oxide to the organic ligand may be 1:3, 1:4, 1:5, 1:6, 1:7, 1:8, 1:9, and etc.

Among them, when the synthesis is carried out in a non-aqueous medium, the molar ratio of the metal atoms to the organic ligands may be as low as 1:2, and the purity of the product is high.

In a specific embodiment of the present invention, the mass ratio of the metal carbonate or oxide to the hydrophilic liquid may be from 1:2 to 1:100. For example, the mass ratio of the metal carbonate or oxide to the hydrophilic liquid may be 1:20, 1:30, 1:40, 1:50, 1:60.

The method for preparing a zeolitic imidazolate framework according to the present invention comprises a step of introducing an acidic gas to reach a pressure of 0.1 MPa to 2.0 MPa in a reactor, and maintaining the pressure for 30 to 60 minutes, and terminating the reaction. The acidic gas is used as a proton agent to interact with a pair of free electrons on the imidazole ring to form a carbonyl group to remove proton hydrogen.

The preparation method according to the present invention reduces the difficulty of deprotonation of the organic ligand by adding an acidic gas as a deprotonating gas, thereby reducing the reaction temperature and the reaction time, allowing the experiment to be carried out under normal temperature and normal pressure, and improving the product yield, and the acidic gas can be completely removed as a reaction gas, and the reaction process is environmentally friendly.

In a specific embodiment of the present invention, the acidic gas used may be $CO_2$, $H_2S$, $SO_2$ or $NO_2$.

In a specific embodiment of the present invention, step 2 is carried out at 10° C. to 40° C.

The method for preparing a zeolitic imidazolate framework according to the present invention comprises a step of heating to 30° C. to 60° C. and vacuuming to obtain the zeolitic imidazolate framework. The acidic gas is removed from the intermediate by appropriate heating and vacuuming, and N atom at 1-position of the resulting 2-methylimidazole ring bonds to the metal ion due to the presence of a lone pair of electrons, and forms ZIFs by self-assembly.

The present invention also provides a zeolitic imidazolate framework which is prepared by the above-described preparation method according to the present invention.

The method for preparing the zeolitic imidazolate framework according to the present invention has the advantages of simple process, low requirements on equipment, simple operation, and can be used for large-scale industrial synthesis.

The method for preparing the zeolitic imidazolate framework according to the present invention has the advantages of high synthesis speed, mild conditions and low energy consumption.

The method for preparing a zeolitic imidazolate framework according to the present invention has high product yield, up to 93%.

The method for preparing the zeolitic imidazolate framework according to the present invention is environmentally friendly, the metal source is metal carbonate or oxide, the by-products are only water and carbon dioxide, and the liquid medium can be recycled without any other by-products and waste fluid.

DETAILED DESCRIPTION OF THE INVENTION

In order to more clearly understand the technical features, objects, and advantageous effects of the present invention, the technical solutions of the present invention are described in detail below, but are not to be construed as limiting the implementable scope of the present invention.

Example 1

This example provided a method for preparing a zeolitic imidazolate framework, comprising the following steps:

1.6843 g of basic zinc carbonate [$ZnCO_3 \cdot 2Zn(OH)_2 \cdot H_2O$] and 7.5294 g of 2-methylimidazole were dissolved in a mixed solution of 7.5885 g of water and 7.5470 g of ethylene glycol, and stirred uniformly;

carbon dioxide was introduced at 25° C. to reach an equilibrium pressure of 0.54 MPa, and the pressure was maintained for 30 minutes, and the reaction was terminated;

then the reactor was heated to 40° C., and vacuumed to remove carbon dioxide;

after $CO_2$ was removed, the solid-liquid mixture was separated by filtration, and the solid phase product was placed in a vacuum drying oven, dried and activated to obtain a ZIF-8 crystal, and finally the filtrate was recycled and reused for the next cycle.

Figure 1:
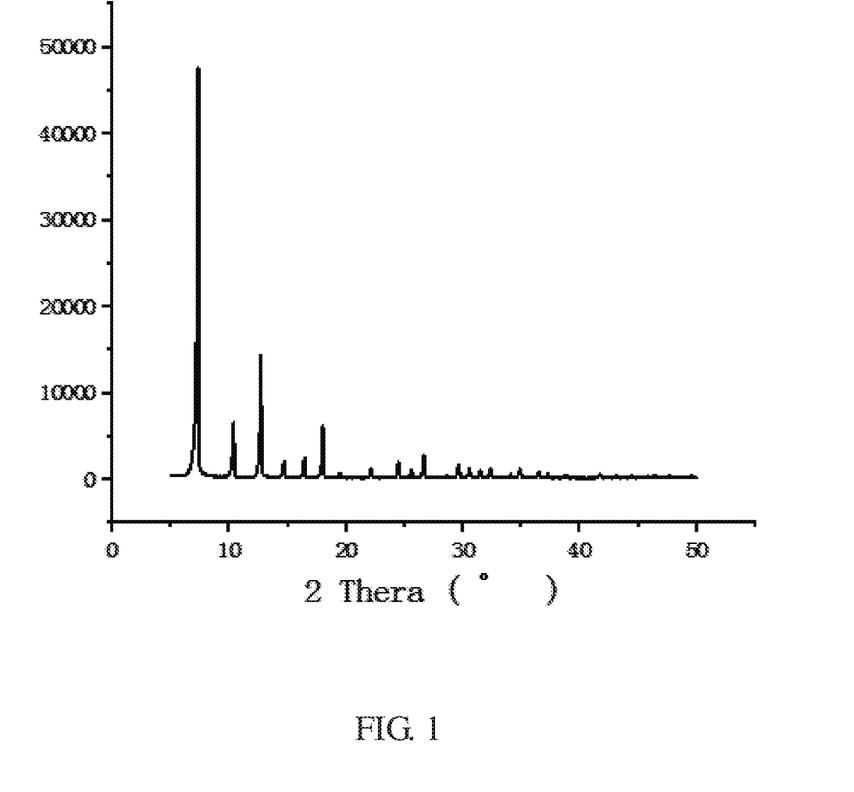
FIG. 1 is an X-ray diffraction (XRD) pattern of a ZIFs crystal synthesized in Example 1 of the present invention.

The XRD peak shape of the ZIF-8 crystal of the example is shown in FIG. 1, which is consistent with the literature report (Yaghi et al, Exceptional chemical and thermal stability of zeolitic imidazolate frameworks, PNAS, 2006, 103 (27):10186-10191). The yield of the ZIF-8 of the example was 93%.

Example 2

This example provided a method for preparing a zeolitic imidazolate framework, comprising the following steps:

1.7105 g of zinc oxide and 4.1258 g of 2-methylimidazole were dissolved in 15.0052 g of methanol, and stirred uniformly;

sulfur dioxide was introduced at 20° C. to reach an equilibrium pressure of 0.65 MPa, and the pressure was maintained for 35 minutes, and the reaction was terminated;

the reactor was heated to 50° C., and vacuumed to remove sulfur dioxide;

after $SO_2$ was removed, the solid-liquid mixture was separated by filtration, and the solid phase product was placed in a vacuum drying oven, dried and activated to obtain a ZIF-8 crystal, and finally the filtrate was recycled and reused for the next cycle.

Figure 2:
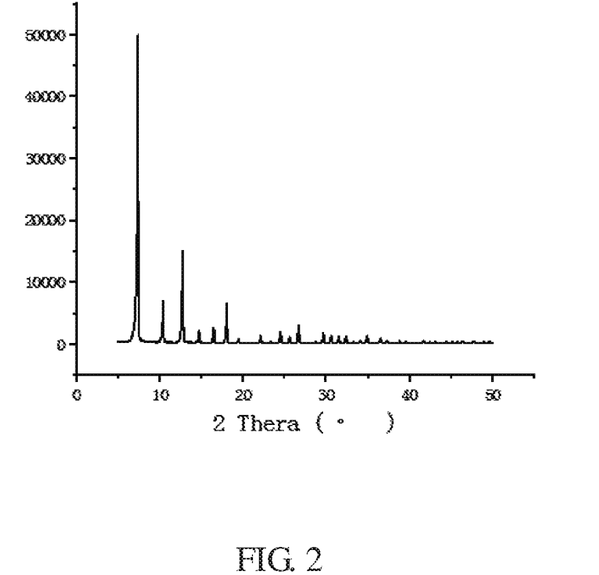
FIG. 2 is an X-ray diffraction (XRD) pattern of a ZIFs crystal synthesized in Example 2 of the present invention.

The XRD peak shape of the ZIF-8 crystal of the example is shown in FIG. 2, which is consistent with the literature report (Yaghi et al, Exceptional chemical and thermal stability of zeolitic imidazolate frameworks, PNAS, 2006, 103 (27):10186-10191). The calculated yield of the example was 90%.

Example 3

This example provided a method for preparing a zeolitic imidazolate framework, comprising the following steps:

6.0365 g of cobalt carbonate and 28.2120 g of 2-methylimidazole were dissolved in 20.0365 g of ethanol and 60.0325 g of DMA, and stirred uniformly;

carbon dioxide was introduced at 27° C. to reach an equilibrium pressure of 0.24 MPa, the pressure was maintained for 50 minutes, and the reaction was terminated;

the reactor was heated to 50° C., and vacuumed to remove carbon dioxide;

after $CO_2$ was removed, the solid-liquid mixture was separated by filtration, and the solid phase product was placed in a vacuum drying oven, dried and activated to obtain a ZIF-67 crystal, and finally the filtrate was recycled and reused for the next cycle.

Figure 3:
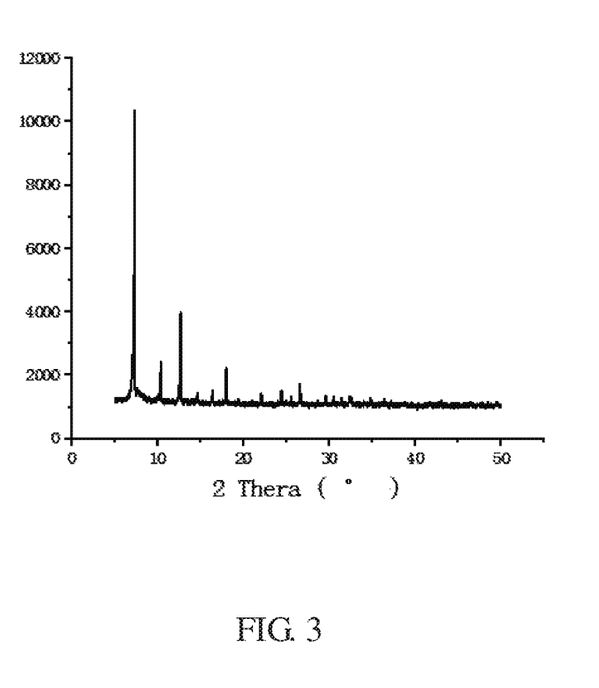
FIG. 3 is an X-ray diffraction (XRD) pattern of a ZIFs crystal synthesized in Example 3 of the present invention.

The XRD peak shape of the crystal of the example is shown in FIG. 3, which is consistent with the literature report (Qian et al. Hydrothermal synthesis of zeolitic imidazolate framework-67 (ZIF-67) nanocrystals, Materials Letters, 2012, 82:220-223). The yield of ZIF-67 of the example was 80%.

Example 4

This example provided a method for preparing a zeolitic imidazolate framework, comprising the following steps:

2.7321 g of basic zinc carbonate [$ZnCO_3 \cdot 2Zn(OH)_2 \cdot H_2O$] and 9.5903 g of 2-ethylimidazole were dissolved in 20.0069 g of water and 30.0052 g of DMF, and stirred uniformly;

carbon dioxide was introduced at 30° C. to reach an equilibrium pressure of 1.50 MPa, and the pressure was maintained for 60 minutes, and the reaction was terminated;

the reactor was heated to 50° C., and vacuumed to remove carbon dioxide;

after $CO_2$ was removed, the solid-liquid mixture was separated by filtration, and the solid phase product was placed in a vacuum drying oven, dried and activated to obtain a ZIF crystal, and finally the filtrate was recycled and reused for the next cycle.

Figure 4:
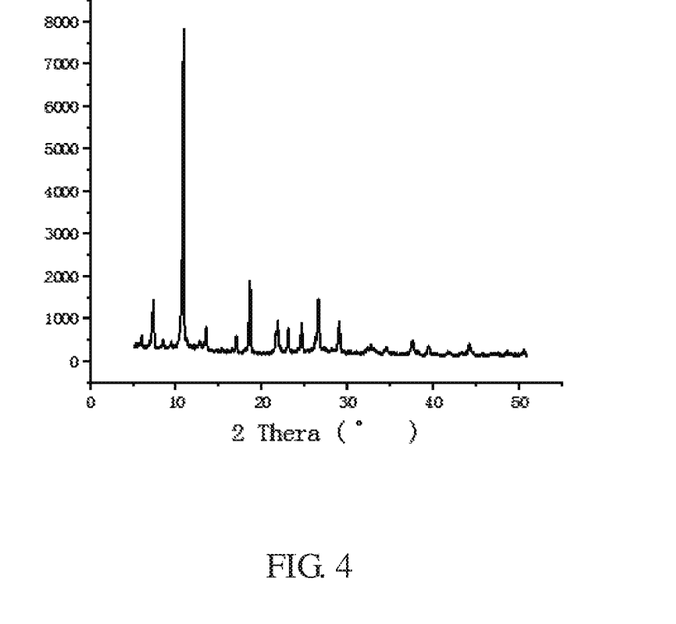
FIG. 4 is an X-ray diffraction (XRD) pattern of a ZIFs crystal synthesized in Example 4 of the present invention.

The XRD peak shape of the ZIF crystal of the example is shown in FIG. 4, and is not reported by any literature. The yield of the ZIF crystal of the example was 83%.

Example 5

This example provided a method for preparing a zeolitic imidazolate framework, comprising the following steps:

1.1243 g of basic zinc carbonate [$ZnCO_3 \cdot 2Zn(OH)_2 \cdot H_2O$] and 4.7494 g of 2-propylimidazole were dissolved in 50.0036 g of water, and stirred uniformly;

nitrogen dioxide was introduced at 28° C. to reach an equilibrium pressure of 0.14 MPa, and the pressure was maintained for 30 minutes, and the reaction was terminated;

the reactor was heated to 40° C., and vacuumed to remove nitrogen dioxide and carbon dioxide;

after $NO_2$ and $CO_2$ was removed, the solid-liquid mixture was separated by filtration, and the solid phase product was placed in a vacuum drying oven, dried and activated to obtain a ZIF crystal, and finally the filtrate was recycled and reused for the next cycle.

Figure 5:
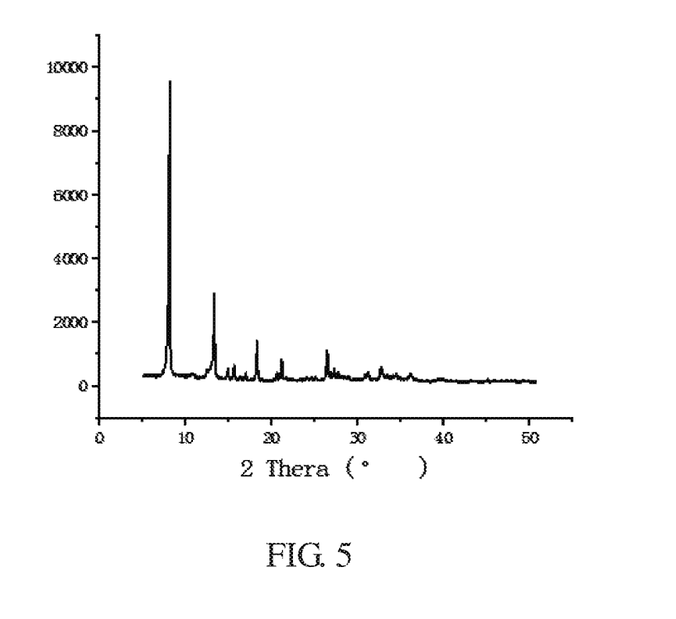
FIG. 5 is an X-ray diffraction (XRD) pattern of a ZIFs crystal synthesized in Example 5 of the present invention.

The XRD peak shape of the ZIF crystal of the example is shown in FIG. 5, and is not reported by any literature. The yield of the ZIF crystal of the example was 81%.

Example 6

This example provided a method for preparing a zeolitic imidazolate framework, comprising the following steps:

1.7103 g of basic zinc carbonate [$ZnCO_3 \cdot 2Zn(OH)_2 \cdot H_2O$] and 4.1283 g of imidazole were dissolved in 50.0135 g of water and stirred uniformly;

sulfur dioxide was introduced at 30° C. to reach an equilibrium pressure of 0.6 MPa, and the pressure was maintained for 55 minutes, and the reaction was terminated;

the reactor was heated to 40° C., and vacuumed to remove sulfur dioxide and carbon dioxide;

after $SO_2$ and $CO_2$ was removed, the solid-liquid mixture was separated by filtration, and the solid phase product was placed in a vacuum drying oven, dried and activated to obtain a ZIF crystal, and finally the filtrate was recycled and reused for the next cycle.

Figure 6:
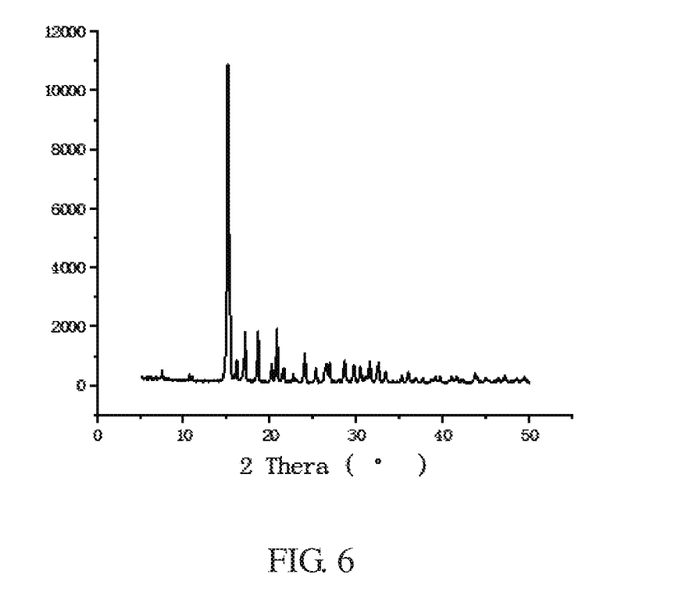
FIG. 6 is an X-ray diffraction (XRD) pattern of a ZIFs crystal synthesized in Example 6 of the present invention.

The XRD peak shape of the ZIF crystal of the example is shown in FIG. 6, and is not reported by any literature. The yield of the ZIF crystal of the example was 74%.

Example 7

This example provided a method for preparing a zeolitic imidazolate framework, comprising the following steps:

0.3852 g of basic zinc carbonate [$ZnCO_3 \cdot 2Zn(OH)_2 \cdot H_2O$] and 1.9720 g of benzimidazole were dissolved in 50.0132 g of DMF and stirred uniformly;

carbon dioxide was introduced at 40° C. to reach an equilibrium pressure of 0.56 MPa, and the pressure was maintained for 40 minutes, and the reaction was terminated;

the reactor was heated to 40° C., and vacuumed to remove carbon dioxide;

after $CO_2$ was removed, the solid-liquid mixture was separated by filtration, and the solid phase product was placed in a vacuum drying oven, dried and activated to obtain a ZIF-7 crystal, and finally the filtrate was recycled and reused for the next cycle.

Figure 7:
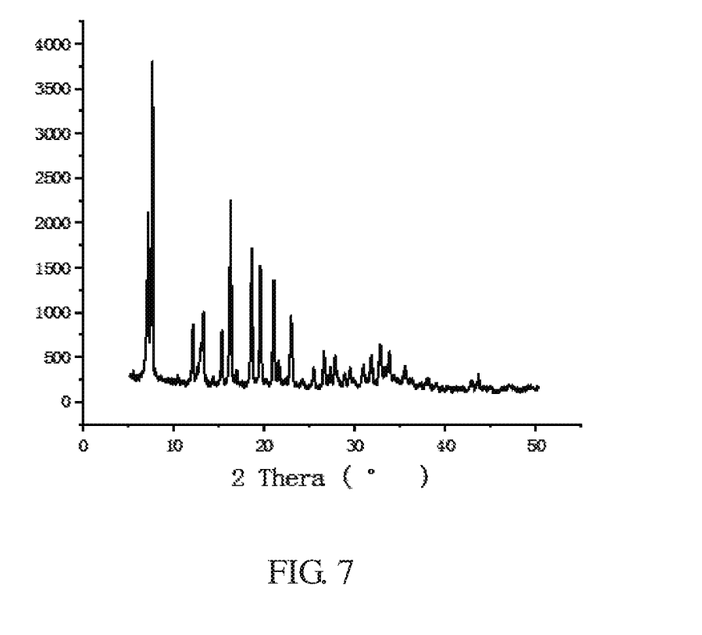
FIG. 7 is an X-ray diffraction (XRD) pattern of a ZIFs crystal synthesized in Example 7 of the present invention.

The XRD peak shape of the ZIF-7 crystal of the example is shown in FIG. 7, which is consistent with the literature report (Yaghi et al, Exceptional chemical and thermal stability of zeolitic imidazolate frameworks, PNAS, 2006, 103 (27):10186-10191). The yield of the ZIF-7 of the example was 80%.

Example 8

This example provided a method for preparing a zeolitic imidazolate framework, comprising the following steps:

0.1842 g of zinc oxide, 0.2623 g of cobalt carbonate and 1.4523 g of 2-methylimidazole were dissolved in 15.0036 g of ethylene glycol and stirred uniformly;

carbon dioxide was introduced at 25° C. to reach an equilibrium pressure of 0.14 MPa, and the pressure was maintained for 30 minutes, and the reaction was terminated;

the reactor was heated to 40° C., and vacuumed to remove carbon dioxide;

after $CO_2$ was removed, the solid-liquid mixture was separated by filtration, and the solid phase product was placed in a vacuum drying oven, dried and activated to obtain a bimetallic Zn/Co-ZIF crystal, and finally the filtrate was recycled and reused for the next cycle.

Figure 8:
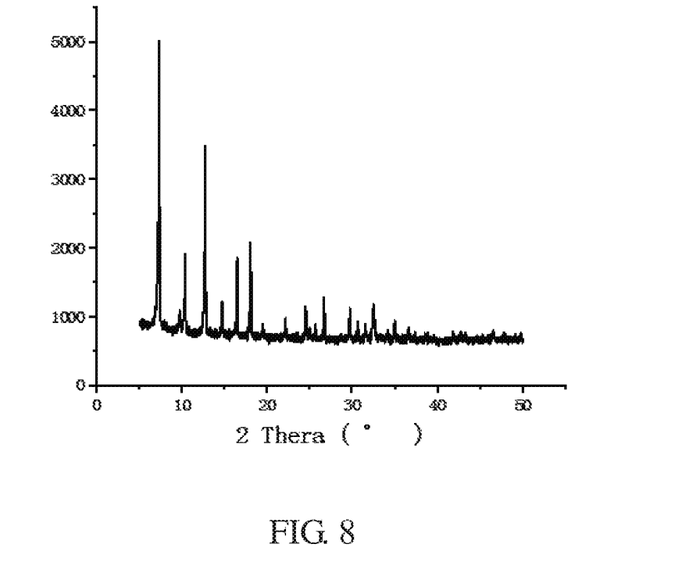
FIG. 8 is an X-ray diffraction (XRD) pattern of a ZIFs crystal synthesized in Example 8 of the present invention.

The XRD peak shape of the bimetallic Zn/Co-ZIF crystal of the example is shown in FIG. 8 and is consistent with ZIF-8/ZIF-67. The yield of the Zn/Co-ZIF crystal of the example was 86%.

Example 9

This example provided a method for preparing a zeolitic imidazolate framework, comprising the following steps:

1.0023 g of zinc oxide, 0.6005 g of imidazole, 0.0023 g of 2-methylimidazole, 0.6032 g of 2-ethylimidazole, and 0.60053 g of 2-propylimidazole were dissolved in 50.0036 g of DMA, and stirred uniformly;

carbon dioxide was introduced at 18.5° C. to reach an equilibrium pressure of 0.14 MPa, and the pressure was maintained for 55 minutes, and the reaction was terminated;

the reactor was heated to 40° C., and vacuumed to remove carbon dioxide;

after $CO_2$ was removed, the solid-liquid mixture was separated by filtration, and the solid phase product was placed in a vacuum drying oven, dried and activated to obtain a composite ZIF crystal, and finally the filtrate was recycled and reused for the next cycle.

Figure 9:
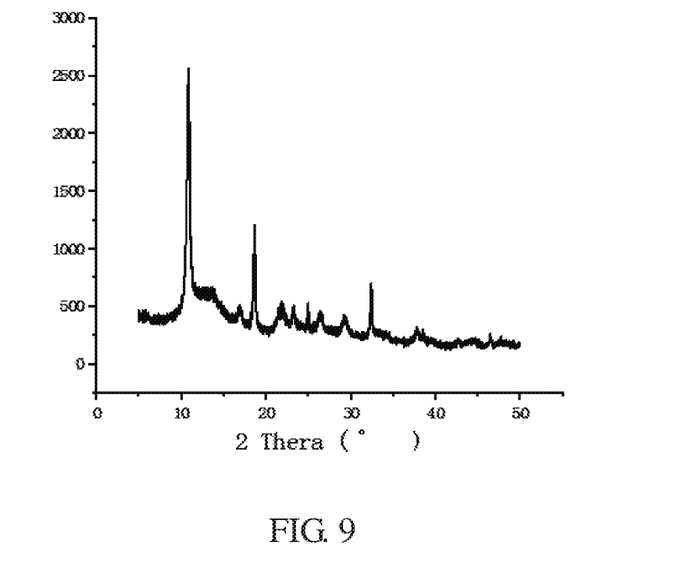
FIG. 9 is an X-ray diffraction (XRD) pattern of a ZIFs crystal synthesized in Example 9 of the present invention.

The XRD peak shape of the composite ZIF crystal of the example is shown in FIG. 9, and the composite crystal has not been reported in the literature yet. The yield of the composite ZIF of the example was 74%.

Example 10

Figure 10:
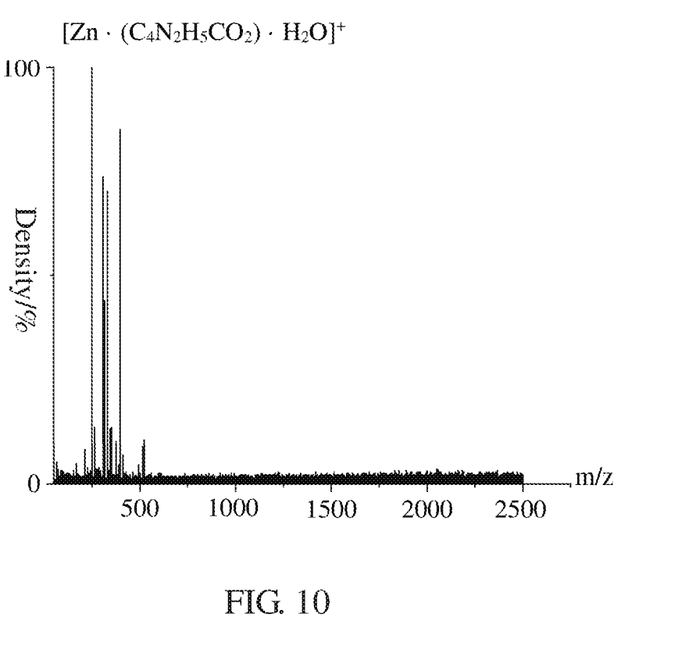
FIG. 10 is a mass spectrum in the process for synthesizing a ZIFs crystal according to Example 10 of the present invention.

In this example, ZIF-8 was synthesized from zinc oxide (ZnO) and 2-methylimidazole in an aqueous medium, specifically comprising the following steps:

3.4202 g of zinc oxide and 8.2501 g of 2-methylimidazole were dissolved in 30.0052 g of water and stirred uniformly;

carbon dioxide was introduced at 25° C. to reach an equilibrium pressure of 0.64 MPa, and the pressure was maintained for 30 minutes, and the reaction was terminated;

the reactor was heated to 50° C., and vacuumed to remove carbon dioxide;

after $CO_2$ was removed, the solid-liquid mixture was separated by filtration, and the solid phase product was placed in a vacuum drying oven, dried and activated to obtain a ZIF-8 crystal, and finally the filtrate was recycled and reused for the next cycle. After introducing CO$_2$, it was found by infrared analysis that a new carbonyl absorption peak appeared at 1639 cm$^{-1}$ after CO$_2$ absorption in the system (TONG Xiongshi, et al. Removal of CO$_2$ from natural gas by 2-methylimidazole/ethylene glycol system at room temperature. CIESC Journal, 2016, 67(10): 4240-4245), indicating that CO$_2$ as a deprotonating agent interacts with the pair of free electron pairs of N on the imidazole ring to form a carbonyl, thereby removing proton hydrogen. The presence of [Zn.(C$_4$N$_2$H$_5$CO$_2$).H$_2$O]$^+$ in the system was determined by mass spectrometry analysis (FIG. 10). Therefore, it is speculated that the removed hydrogen ions react with zinc oxide to form water, and zinc ions are combined with the ligand having a carbonyl group to form the intermediate Zn.(C$_4$N$_2$H$_5$CO$_2$), which is then complexed with solvent water to form [Zn.(C$_4$N$_2$H$_5$CO$_2$).H$_2$O], thus continuously consumes zinc oxide. The mechanism is shown as follows:

CO$_2$ is removed from the Zn(C$_4$N$_2$H$_5$CO$_2$)$^+$ intermediate by appropriate heating and vacuuming, to form Zn(C$_4$N$_2$H$_5$)$^+$, and N atom at 1-position of the resulting 2-methylimidazole ring bonds to Zn ion due to the presence of a lone pair of electrons, and forms ZIF-8 by self-assembly. The mechanism is shown as follows.

Example 11

In this example, ZIF-67 was synthesized from cobalt carbonate (CoCO$_3$) and 2-methylimidazole in an aqueous medium, specifically comprising the following steps:

3.0335 g of cobalt carbonate and 14.1120 g of 2-methylimidazole were dissolved in 40.0353 g of water and stirred uniformly;

carbon dioxide was introduced at 26° C. to reach an equilibrium pressure of 0.26 MPa, and the pressure was maintained for 30 minutes, and the reaction was terminated;

the reactor was heated to 50° C., and vacuumed to remove carbon dioxide;

after CO$_2$ was removed, the solid-liquid mixture was separated by filtration, and the solid phase product was placed in a vacuum drying oven, dried and activated to obtain a ZIF-67 crystal, and finally the filtrate was recycled and reused for the next cycle. The mechanism is shown as follows:

Example 12

This example provided a method for preparing a zeolitic imidazolate framework, comprising the following steps:

0.8422 g of basic zinc carbonate [ZnCO$_3$.2Z(OH)$_2$.H$_2$O] and 1.2123 g of 2-methylimidazole were dissolved in the recycled filtrate of Example 1, and stirred uniformly;

carbon dioxide was introduced at 25° C. to reach an equilibrium pressure of 0.54 MPa, and the pressure was maintained for 30 minutes, and the reaction was terminated;

then the reactor was heated to 40° C., and vacuumed to remove carbon dioxide;

after CO$_2$ was removed, the solid-liquid mixture was separated by filtration, and the solid phase product was placed in a vacuum drying oven, dried and activated to obtain a ZIF-8 crystal, and finally the filtrate was recycled and reused for the next cycle.

Figure 11:
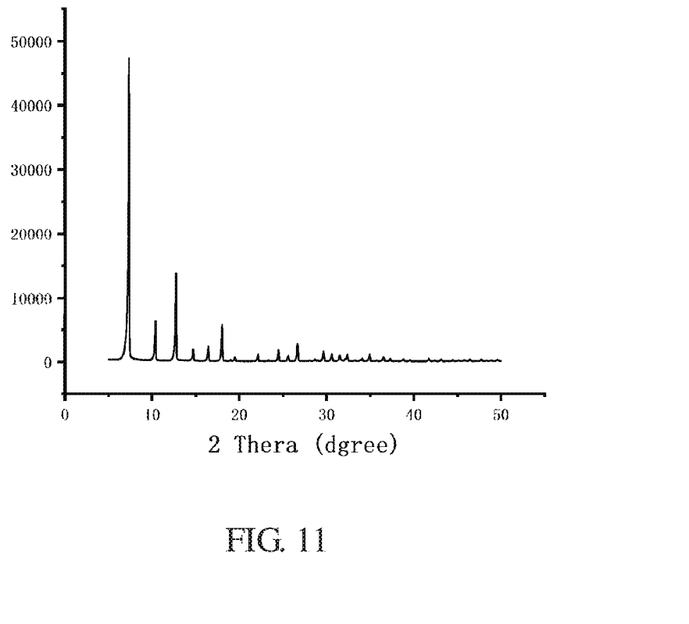
FIG. 11 is an X-ray diffraction (XRD) pattern of a ZIFs crystal synthesized in Example 12 of the present invention.

The XRD peak shape of the ZIF-8 crystal of the example is shown in FIG. 11, which is consistent with the literature report (Yaghi et al, Exceptional chemical and thermal stability of zeolitic imidazolate frameworks, PNAS, 2006, 103 (27):10186-10191). The yield of the ZIF-8 of the example was 91%.

What is claimed is:

1. A method for preparing a zeolitic imidazolate framework, characterized in that the method comprises the following steps:

Step 1: adding a metal carbonate or oxide and an organic ligand to a hydrophilic liquid to obtain a mixture;

Step 2: introducing an acidic gas to reach a reaction pressure of 0.1 MPa to 2.0 MPa, maintaining the pressure for 30 to 60 minutes, and terminating the reaction;

Step 3: heating to 30° C.–60° C. and vacuuming to obtain the zeolitic imidazolate framework,
wherein the hydrophilic liquid comprises one or a combination of two or more of water, an alcohol, and an amide;
wherein the acidic gas is $CO_2$, $H_2S$, $SO_2$, or $NO_2$; and
wherein the organic ligand is selected from the group consisting of one or a combination of two or more of imidazole, 2-methylimidazole, 2-ethylimidazole, 2-propylimidazole, and benzimidazole.

2. The preparation method according to claim 1, characterized in that a mass ratio of the metal carbonate or oxide to the hydrophilic liquid is 1:2 to 1:100.

3. The preparation method according to claim 1, characterized in that a molar ratio of the metal atom in the metal carbonate or oxide to the organic ligand is 1:2 to 1:10.

4. The preparation method according to claim 1, characterized in that the hydrophilic liquid comprises water, an aqueous solution of an alcohol, an aqueous solution of an amide, or an alcoholic solution of an amide.

5. The preparation method according to claim 4, characterized in that the alcohol comprises methanol, ethanol, ethylene glycol, or triethylene glycol.

6. The preparation method according to claim 4, characterized in that the amide comprises N,N-dimethylformamide, N,N-dimethylacetamide, or N,N-diethylformamide.

7. The preparation method according to claim 1, characterized in that Steps 1 and 2 are carried out at 10° C. to 40° C.

8. The preparation method according to claim 1, characterized in that the metal carbonate or oxide is selected from the group consisting of one or a combination of two of basic zinc carbonate, cobalt carbonate, zinc oxide, and cobalt oxide.

* * * * *